(12) United States Patent
Nanjyo et al.

(10) Patent No.: US 7,951,126 B2
(45) Date of Patent: May 31, 2011

(54) ABSORBENT ARTICLE

(75) Inventors: Ayako Nanjyo, Fuji (JP); Yasuo Ido, Shioya-gun (JP)

(73) Assignee: Daio Paper Corporation, Ehime (JP)

( * ) Notice: Subject to any disclaimer, the term of this patent is extended or adjusted under 35 U.S.C. 154(b) by 290 days.

(21) Appl. No.: 10/573,214

(22) PCT Filed: Sep. 30, 2004

(86) PCT No.: PCT/JP2004/014389
§ 371 (c)(1),
(2), (4) Date: Mar. 24, 2006

(87) PCT Pub. No.: WO2005/030103
PCT Pub. Date: Apr. 7, 2005

(65) Prior Publication Data
US 2008/0183150 A1    Jul. 31, 2008

(30) Foreign Application Priority Data

Sep. 30, 2003 (JP) .................................. 2003-339086

(51) Int. Cl.
*A61F 13/15* (2006.01)

(52) U.S. Cl. ............... 604/385.101; 604/365; 604/381; 604/378; 604/366; 156/154; 156/566; 156/301; 156/292; 156/291; 156/298; 156/299; 156/300; 156/302; 156/324

(58) Field of Classification Search .................. 604/365, 604/381, 378, 366, 385
See application file for complete search history.

(56) References Cited

U.S. PATENT DOCUMENTS

| | | | | |
|---|---|---|---|---|
| 5,795,345 A | * | 8/1998 | Mizutani et al. | 604/380 |
| 5,807,363 A | * | 9/1998 | Hamajima et al. | 604/366 |
| 5,891,118 A | * | 4/1999 | Toyoshima et al. | 604/366 |
| 6,410,822 B1 | * | 6/2002 | Mizutani | 604/380 |
| 6,436,082 B1 | | 8/2002 | Mizutani et al. | |
| 6,563,013 B1 | * | 5/2003 | Murota | 604/380 |
| 6,858,771 B2 | * | 2/2005 | Yoshimasa et al. | 604/380 |
| 6,867,345 B2 | * | 3/2005 | Shimoe et al. | 604/378 |

FOREIGN PATENT DOCUMENTS

| | | |
|---|---|---|
| JP | 60-120953 | 8/1985 |
| JP | 8-117277 | 5/1996 |
| JP | 10-328232 | 12/1998 |
| JP | 11-358 | 1/1999 |
| JP | 11-033054 | 2/1999 |
| JP | 2000-83994 | 3/2000 |
| JP | 2001-137284 | 5/2001 |
| JP | 2002-345888 | 12/2002 |
| JP | 2003-230593 | 8/2003 |

* cited by examiner

*Primary Examiner* — Tatyana Zalukaeva
*Assistant Examiner* — Ilya Y Treyger
(74) *Attorney, Agent, or Firm* — Jordan and Hamburg LLP (57) ABSTRACT

An absorbent article is disclosed in which an absorbent body intervenes between a liquid permeable front sheet and a back sheet. A middle-height portion is provided by thickening a front surface of an approximately center area of the absorbent body with respect to a standard portion absorbent body. The article includes leakage preventing grooves which extend to a longitudinal direction of the absorbent article are provided on both sides which sandwich a body fluid discharge portion area in the area of the middle-height portion, respectively.

19 Claims, 7 Drawing Sheets fig 1 fig 2 fig 3 fig 4 fig 5 fig 6 fig 7 fig 8 fig 9

ABSORBENT ARTICLE

BACKGROUND OF THE INVENTION

The present invention relates to an absorbent article which is used mainly for sanitary napkins, vaginal discharge sheets, incontinence pads, medical pads, toiletries and the like, and more specifically, relates to the absorbent article which securely prevents sideways leakage of body fluid by improving a blocking effect of a leakage preventing groove.

Conventionally, as absorbent articles such as a panty liner, a sanitary napkin and incontinence pad, substances where an absorbent body made of cotton-like pulp or the like intervenes between a liquid impermeable back sheet such as a polyethylene sheet or a polyethylene sheet-laminated unwoven fabric and a liquid permeable front sheet such as an unwoven fabric or a liquid permeable plastic sheet are known.

Figure 8:
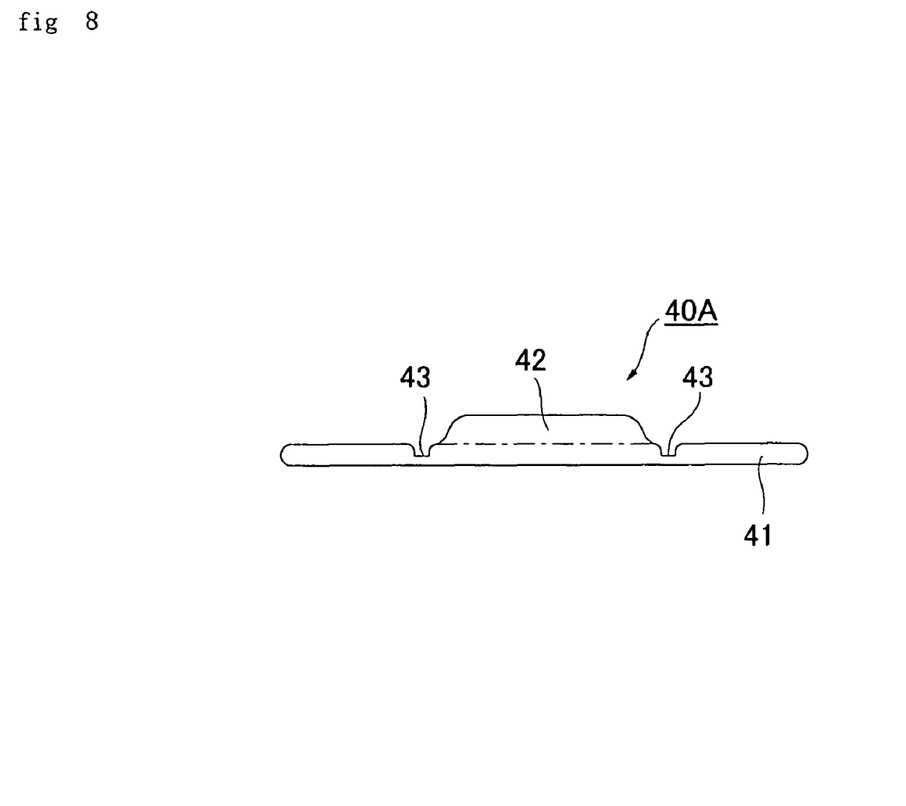
FIG. 8 is a schematic cross sectional view illustrating a conventional absorbent article 40A.
Figure 9:
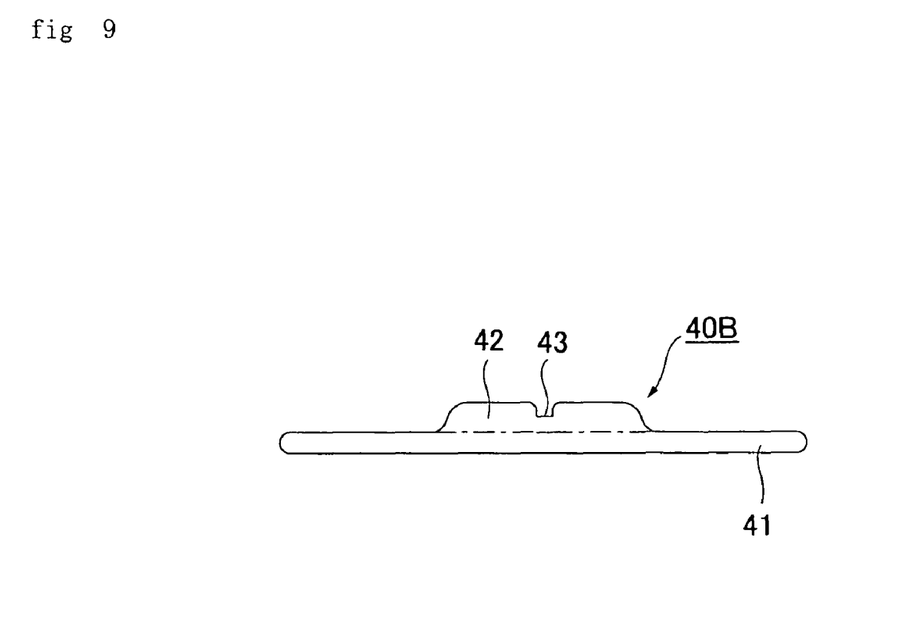
FIG. 9 is a schematic cross sectional view illustrating an conventional absorbent article 40B.

Such kinds of absorbent articles are improved a lot, and various countermeasures for preventing a leakage of body fluid are taken. As one of these body fluid leakage preventing means, as shown in FIG. 8, an absorbent article 40A, in which a middle-height portion 42 is formed on an approximately center area of an absorbent body 41 with its thickness being increased on the surface side so that fitting property to a blood discharge portion is improved, and in order to maintain the shape of the middle-height portion 42 and block body fluid absorbed by the absorbent body 41, an outside position of a peripheral edge of the middle-height portion 42 is subject to cotton-like embossing so that a concave leakage preventing groove 43 is formed, is known (see the following patent documents 1 to 4). Further, as shown in FIG. 9, an absorbent article 40B, in which the center of the middle-height portion 42 is subject to emboss which extends to a longitudinal direction of a napkin so that a leakage preventing groove 43 is formed, is known.

Patent document 1: Japanese Patent Application Laid-Open No. 8-117277
Patent document 2: Japanese Patent Application Laid-Open No. 10-328233
Patent Document 3: Japanese Patent Application Laid-Open No. 11-358
Patent Document 4: Japanese Patent Application Laid-Open No. 11-33054

BRIEF SUMMARY OF THE INVENTION

In the absorbent article 40A, however, since the product is easily fitted to a blood discharge port by forming the middle-height portion 42, a leakage of body fluid to a front-rear direction of the product can be prevented but since the leakage preventing groove 43 is formed on an outside of the middle-height portion 42, namely, a thin portion of the absorbent body 41, the leakage preventing groove 43 cannot be deeply formed, and thus a sideways leakage of body fluid diffusing to a widthwise direction of the product cannot be sufficiently blocked. This problem becomes more serious in the thin-type absorbent articles in which the thickness of the absorbent bodies are thinner.

On the other hand, in the case of the absorbent article 40B which is formed with the leakage preventing groove 43 at the center of the middle-height portion 42, when a lot of body fluid is discharged at a time due to abdominal pressure caused by changing a posture such as moving legs in lying-down and sitting postures or the like, the leakage preventing groove 43 cannot sufficiently store the body fluid, and thus the body fluid overflows so as to leak.

It is, therefore, a main object of the present invention to provide an absorbent article where even if a lot of body fluid is discharged at a time, the body fluid can be sufficiently blocked, and not only a leakage of the body fluid to a front-rear direction but also a sideways leakage to a widthwise direction of the product can be prevented.

In order to solve the problems, the present invention from a first aspect provides an absorbent article in which an absorbent body intervenes between a liquid permeable front sheet and a back sheet, and a middle-height portion is provided by thickening a front surface of an approximately center area of the absorbent body with respect to a standard portion absorbent body, characterized in that leakage preventing grooves which extend to a longitudinal direction of the absorbent article are provided on both sides which sandwich a body fluid discharge portion area in the area of the middle-height portion, respectively.

In the case of the conventional absorbent article shown in FIG. 8, since the outside of the middle-height portion is subject to emboss, the leakage preventing grooves cannot be deeply formed, but according to the present invention from the first aspect, since the width of the middle-height portion is increased and the leakage preventing grooves are formed in the area of the middle-height portion, the sufficient depth of the grooves can be secured, and a lot of body fluid can be stored in the grooves. For this reason, not only front-rear leakage but also sideways leakage of the body fluid can be effectively prevented.

The present invention from a second aspect provides the absorbent article depending from the first aspect, wherein the leakage preventing grooves are deeper than a thickness of the middle-height portion and reach the standard portion absorbent body.

The present invention from a third aspect provides the absorbent article depending from any one of the first and the second aspects, wherein a thinned portion obtained by thinning the middle-height portion by press is formed on outsides of the leakage preventing grooves.

In the invention from the third aspect, the thinned portion is formed on the outsides of the leakage preventing grooves by thinning the middle-height portion by means of press. Therefore, even if the middle-height portion is present, both the sides are thinned by press so that uncomfortable feeling at the time of attachment is eliminated and the folded product can be thinned.

The present invention from a fourth aspect provides the absorbent article depending from any one of first to third aspects, wherein the middle-height portion is formed between front and rear folding line positions for folding the absorbent article in three at the time of individual packaging.

In the invention from the fourth aspect, the middle-height portion is formed between the front and rear folding lines at the time of folding the absorbent article in three at the time of individual packaging. The absorbent article as the product folded in three, is therefore, made to be thin.

The present invention from a fifth aspect provides the absorbent article depending from any one of first to fourth aspects, wherein a thickness of the standard portion absorbent body is 1 to 3 mm.

According to the present invention, even if a lot of body fluid is discharged at a time, the body fluid can be sufficiently blocked, and the leakage to the front-rear direction of the product but also the sideways leakage of the fluid body to the widthwise direction can be prevented. Further, since the outside of the middle-height portion is thinned by press forming, uncomfortable feeling at the time of attaching can be reduced, and since the middle-height portion is formed between lines for folding in three, the thickness can be reduced in a product form.

BRIEF DESCRIPTION OF THE DRAWINGS

Accompanying the specification are figures which assist in illustrating the embodiments of the invention, in which.

DETAILED DESCRIPTION OF THE INVENTION

Embodiments of the present invention are explained in detail below with reference to the drawings.

First Embodiment

Figure 1:
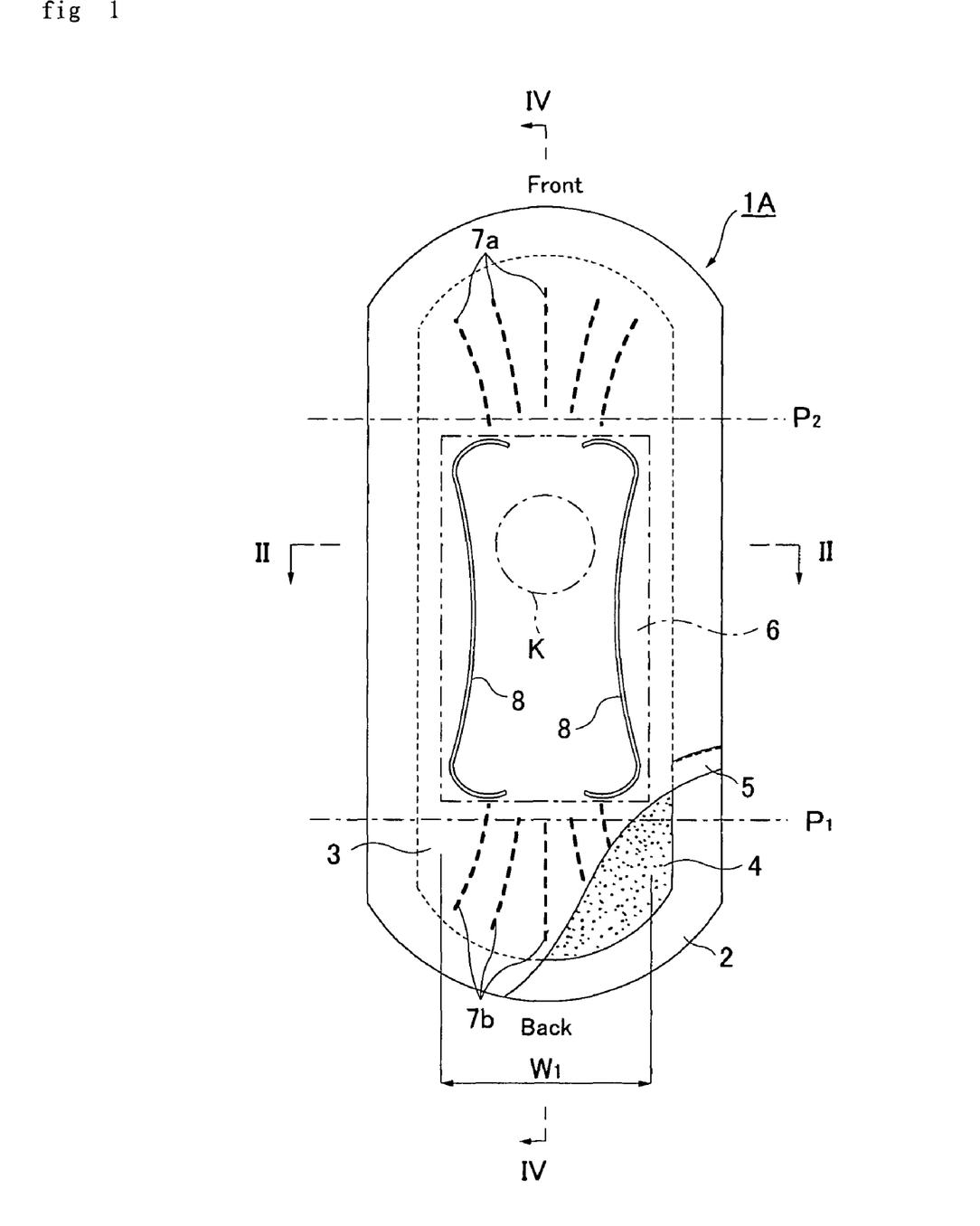
FIG. 1 is partially fracture plan view illustrating an absorbent article 1A according to a first embodiment of the present invention.
Figure 2:
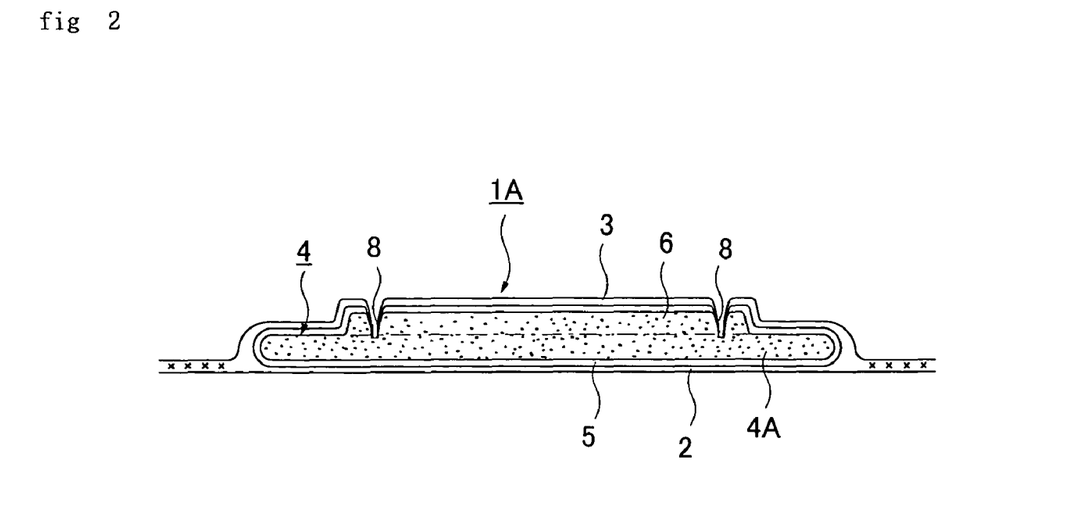
FIG. 2 is a fragmentary view taken along line II-II of FIG. 1.

FIG. 1 is a partially fracture plan view of an absorbent article 1A according to a first embodiment of the present invention, and FIG. 2 is a fragmentary view taken along line II-II of FIG. 1.

The absorbent article 1A is supplied for applications mainly of panty liners, sanitary napkins, vaginal discharge sheets, incontinence pads and the like, and as shown in FIG. 1 for example, it is constituted so that an absorbent body 4 or, as shown in FIG. 1, an absorbent unit, which is composed of the absorbent body 4 and crepe paper 5 surrounding the absorbent body 4, intervenes between a liquid impermeable back sheet 2 and a liquid permeable front sheet 3 (hereinafter, simply front sheet). The liquid impermeable back sheet 2 and the liquid permeable front sheet 3 are jointed by a bonding means such as a hot-melt adhesive around the absorbent body 4.

The liquid impermeable back sheet 2 adopts a sheet material having at least an impervious property made of polyethylene or polypropylene, but a laminate unwoven fabric where unwoven fabrics are laminated on a polyethylene sheet or the like, an unwoven sheet where a waterproof film is provided and thus liquid impermeability is substantially secured (in this case, the liquid impermeable back sheet is composed of the waterproof film and the unwoven fabric), and the like can be used. In recent years, materials having moisture permeability tend to be used preferably in view of stuffiness prevention. As this impervious and moisture permeable sheet material, a fine porous sheet, which is obtained in such a manner that inorganic bulking agent is molten and kneaded into olefin resin such as polyethylene or polypropylene and a sheet is formed, and the sheet is stretched monoxially or biaxially, is suitably used.

As the absorbent body 4, a material which absorbs and keeps body fluid may be used, and normally a material which is obtained by mixing absorbent polymer powder in fluff pulp is used preferably in view of the absorbent function and the price. The pulp is made of cellulose fiber such as chemical pulp obtained by timer or molten pulp, or artificial cellulose fiber such as rayon or acetate, and softwood pulp whose fiber length is longer than hardwood pulp is used preferably from the viewpoint of the function and the price. The absorbent body 4 is preferably surrounded by the crepe paper 5 in order to maintain the shape, quickly diffuse menstrual blood or the like and prevent reverse flow of the menstrual blood which is once absorbed. Further, as shown in the drawing, the plane shape of the absorbent body 4 may have an oval shape or a fit-cut shape (lageniform shape) in order to relieve butting against a groin portion.

On the other hand, as the front sheet 3 in the absorbent article 1A, imperforate or perforated unwoven fabric or porous plastic sheet is used preferably. As a material fiber composing the unwoven fabric, synthetic fiber of olefin, such as polyethylene or polypropylene, polyester, polyamide or the like, regenerated fiber such as rayon or cupra, and natural fiber such as cotton can be used. Further, conjugated fiber such as core-in-sheath fiber whose core is fiber with high melting point and whose sheath is fiber with low melting point, side-by-side fiber and split fiber can be used preferably.

The unwoven fabric which is obtained by the suitable processing methods such as a spun lace method, a spun bond method, a thermal bond method, a melt blown method, a needle punch method can be used. In these processing method, the spun lace method is excellent in flexibility and in a drape property, and the thermal bond method is excellent in bulkiness and softness. Further, the unwoven fabric composed of synthetic fiber is used preferably because this is easily subject to emboss.

Figure 3:
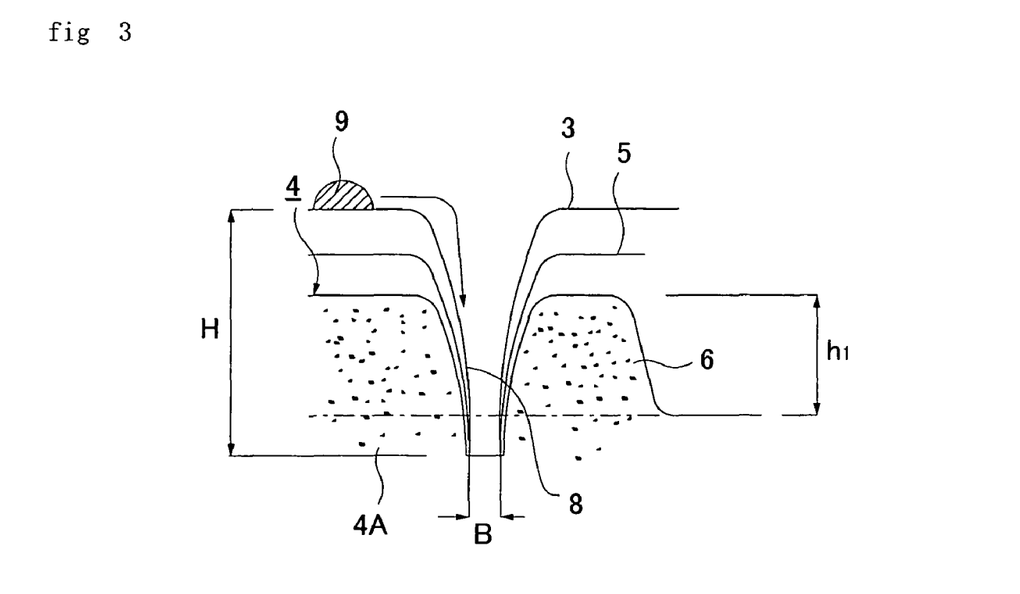
FIG. 3 is an enlarged diagram illustrating a leakage preventing groove 8.
Figure 4:
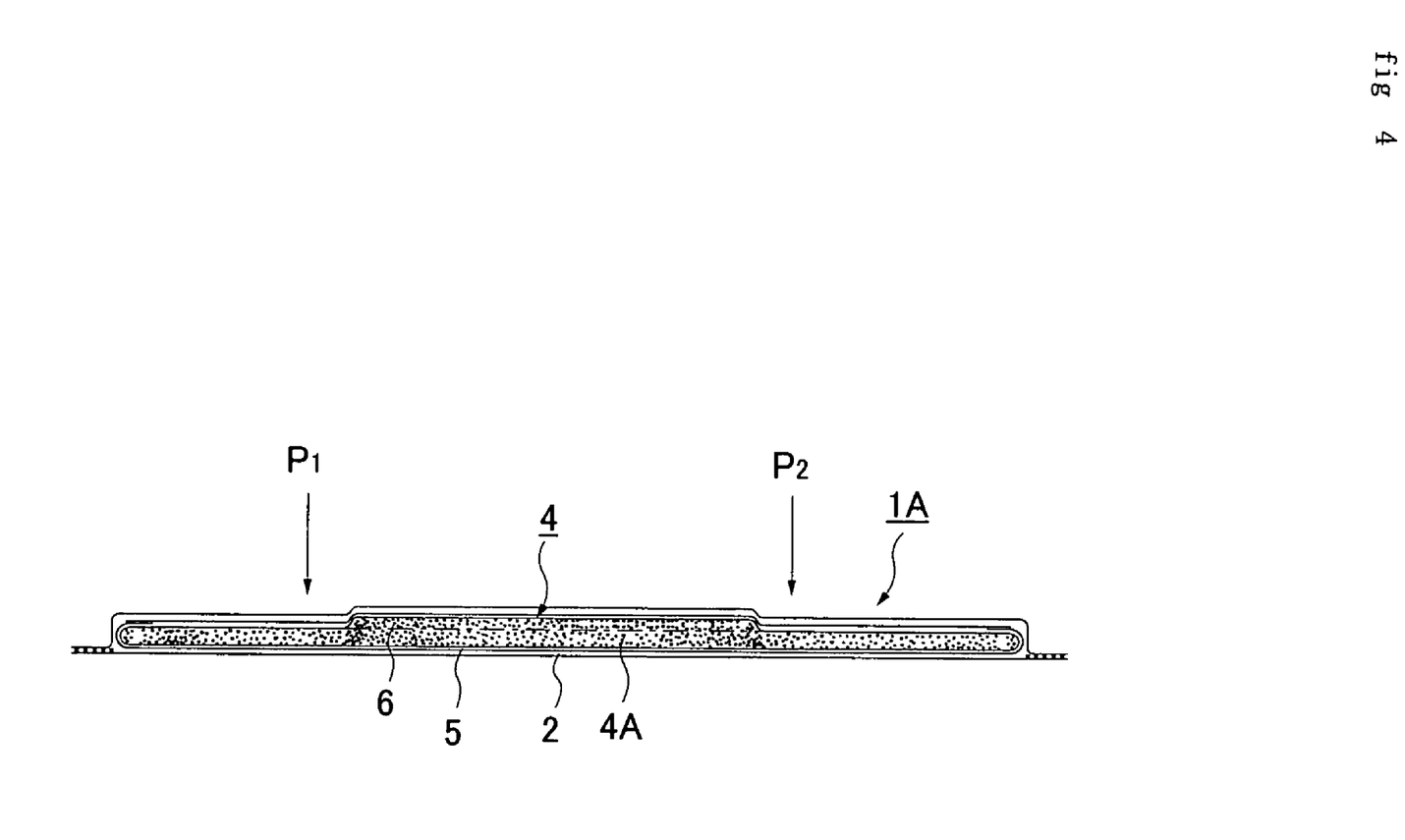
FIG. 4 is a fragmentary view illustrating IV-IV of FIG. 1.

As shown in FIGS. 2 and 3 clearly, the front surface in the approximately center area of the absorbent body 4 has a middle-height portion 6 which is obtained by increasing the thickness of the front surface with respect to a standard portion absorbent body 4A. As shown in FIG. 1, the middle-height portion 6 is formed between front and back folding line positions P1 and P2 to be creases at the time of folding the product. A plurality of side embosses 7a and 7b which extend to an approximately longitudinal direction of the product are formed in vicinities of front and rear ends of the middle-height portion 6. Further, the thickness of the standard portion absorbent body 4A is 1 to 3 mm, and the thickness of the middle-height portion 6 is 1.5 to 8.0 mm, preferably 2.0 to 4.0 mm. Further, as the standard portion absorbent body 4A, air laid fabric or laminated fiber absorbent body which is pressed is desirably used, and the middle-height portion 6 may be formed by laminating individual absorbent sheets or may be formed integrally with the standard portion absorbent body 4A.

Both side portions which sandwich a body fluid discharge area K are embossed from the upper surface of the liquid permeable front sheet 3 in the area of the middle-height portion 6, so that a pair of right and left concave leakage preventing grooves 8, 8 which extend to the longitudinal direction of the product are formed. As shown in FIGS. 2 and 3, the liquid permeable front sheet 3 and the crepe paper 5 are fused by the embossment, so that the leakage preventing grooves 8 are formed so as to be deeper than a thickness h1 of the middle-height portion 6 and covers the standard portion absorbent body 4A. A depth H of the leakage preventing groove 8 is 0.5 to 9.0 mm, preferably 2.0 to 6.0 mm. When the depth H is less than 0.5 mm, the effect for blocking body fluid is small, and thus the sideways leakage cannot be effectively prevented. When the depth H exceeds 9.0 mm, the thickness of the absorbent body should be increased, and thus convenience of the thin absorbent article is lost. Further, a ratio (H/T) of the depth H of the leakage preventing groove 8 to the thickness T of the standard portion absorbent body 4A is 0.06 to 3.3, preferably 0.2 to 0.8. On the other hand, a bottom width B of the leakage preventing groove 8 may be 0.5 to 5.0 mm.

As shown in FIG. 3, in the leakage preventing groove 8, body fluid 9 which is discharged from a body fluid discharge portion (not shown) of a wearer flows thereinto and is blocked so as not to move sideways. That is to say, in the absorbent article 1A, since the leakage preventing groove 8 is formed within the range of the middle-height portion 6 so as to be formed deeply. Furthermore, since a pair of right and left leakage preventing grooves 8 are formed on the outside of the body fluid discharge portion K, even if body fluid flows to both right and left directions, it can be blocked.

The plane shapes of the leakage preventing grooves 8, 8 are not particularly limited as long as they are formed on both the sides which sandwich the body fluid discharge portion K and extend to the longitudinal direction of the product. In the example shown in FIG. 1, however, the plane shape is a curved shape such that the center portion has the narrowest width and their separating width gradually becomes wider on portions which are closer to the front and back ends of the products, and curved portion towards the inner side is formed on the end portions.

Second Embodiment

Figure 5:
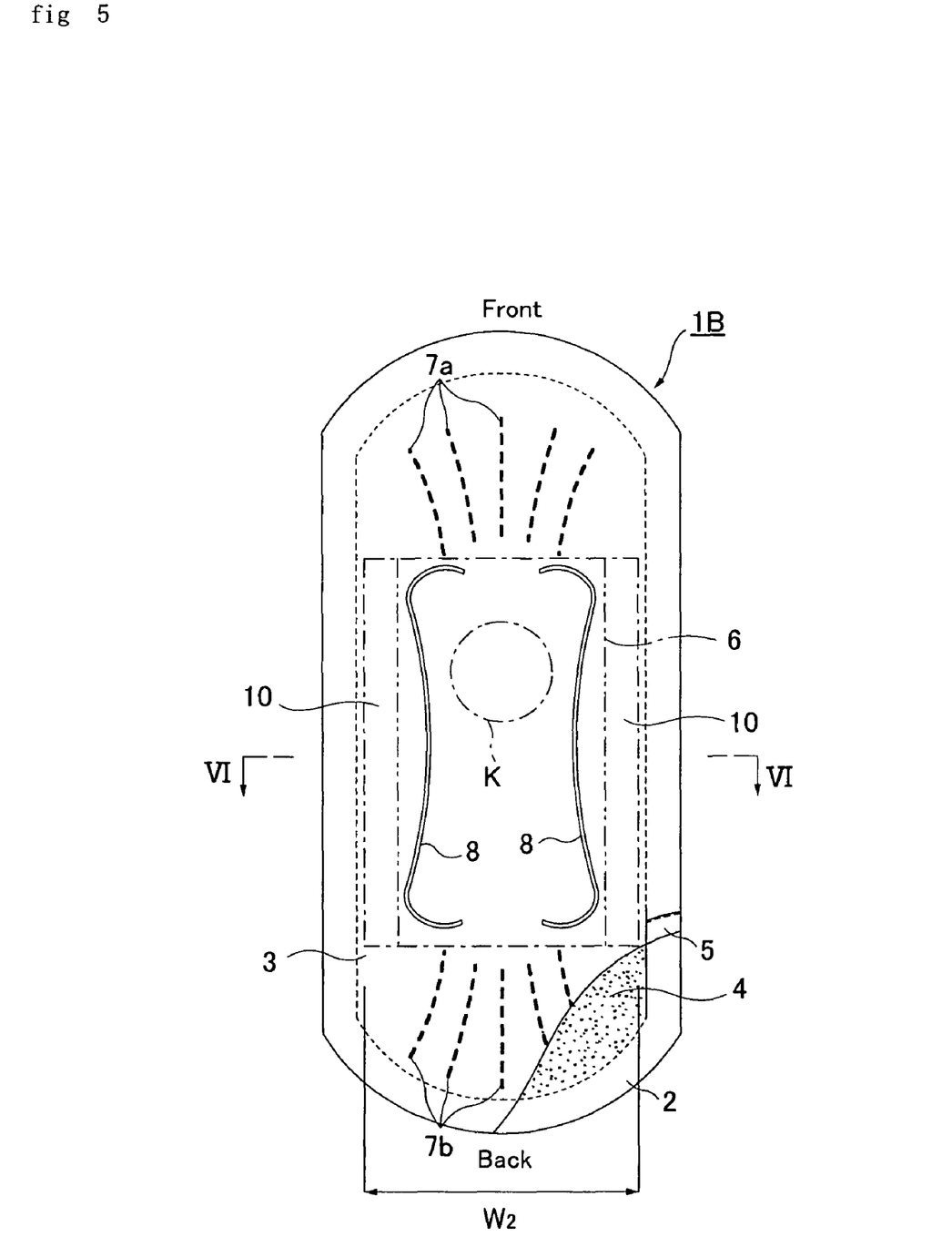
FIG. 5 is a partially fracture plan view illustrating an absorbent article 1B according to a second embodiment of the present invention.
Figure 6:
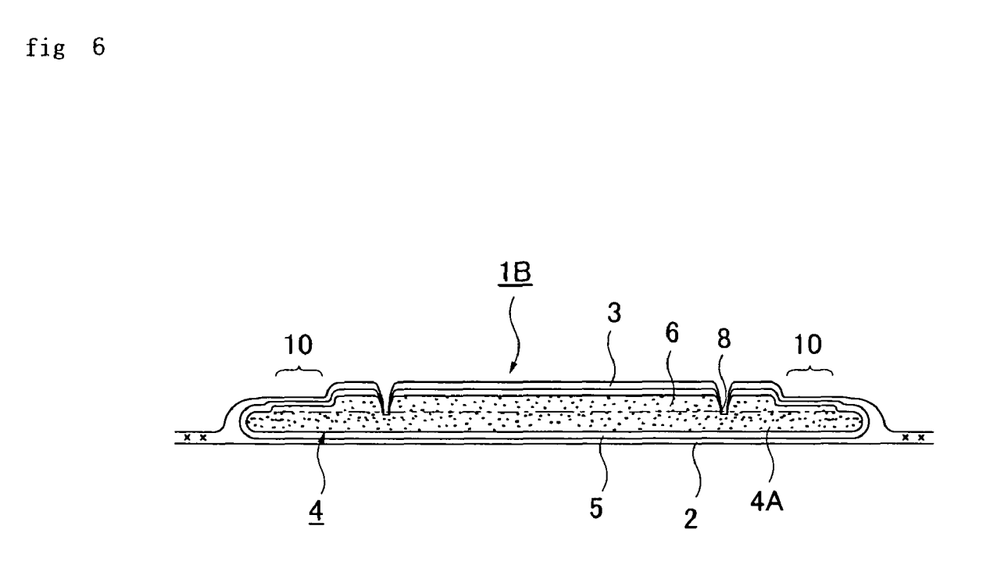
FIG. 6 is a fragmentary view taken along line VI-VI of FIG. 5.

The absorbent article 1B according to a second embodiment shown in FIGS. 5 and 6 is explained in detail below.

The absorbent article 1B is compared with the absorbent article 1A according to the first embodiment, and only a difference is explained. In the absorbent article 1B, as shown in FIG. 5, the width W2 of the middle-height portion 6 is wider than the width W1 (see FIG. 1) of the middle-height portion of the absorbent article 1A, the both sides which sandwich the body fluid discharge portion K are embossed from the upper surface of the liquid permeable front sheet 3 so that a pair of right and left concave leakage preventing grooves 8, 8 are formed in the area of the middle-height portion 6, and the middle-height portion 6 is thinned by pressing so that the thinned portion 10 is formed on the outsides of the leakage preventing grooves 8.

In the absorbent article 1B, since the thinned portion 10 is formed on the outsides of the leakage preventing grooves 8 by press, uncomfortable feeling due to abutting of the side portions of the middle-height portion 6 against a groin portion can be eliminated at the time of attachment.

The thinned portion 10 is not thinned by pressing from the upper side of the liquid permeable front sheet 3, but it is desirable that the single absorbent body is pressed and the thinned portion by means of the pressing is not noticeable from the outside of the product.

Third Embodiment

Figure 7:
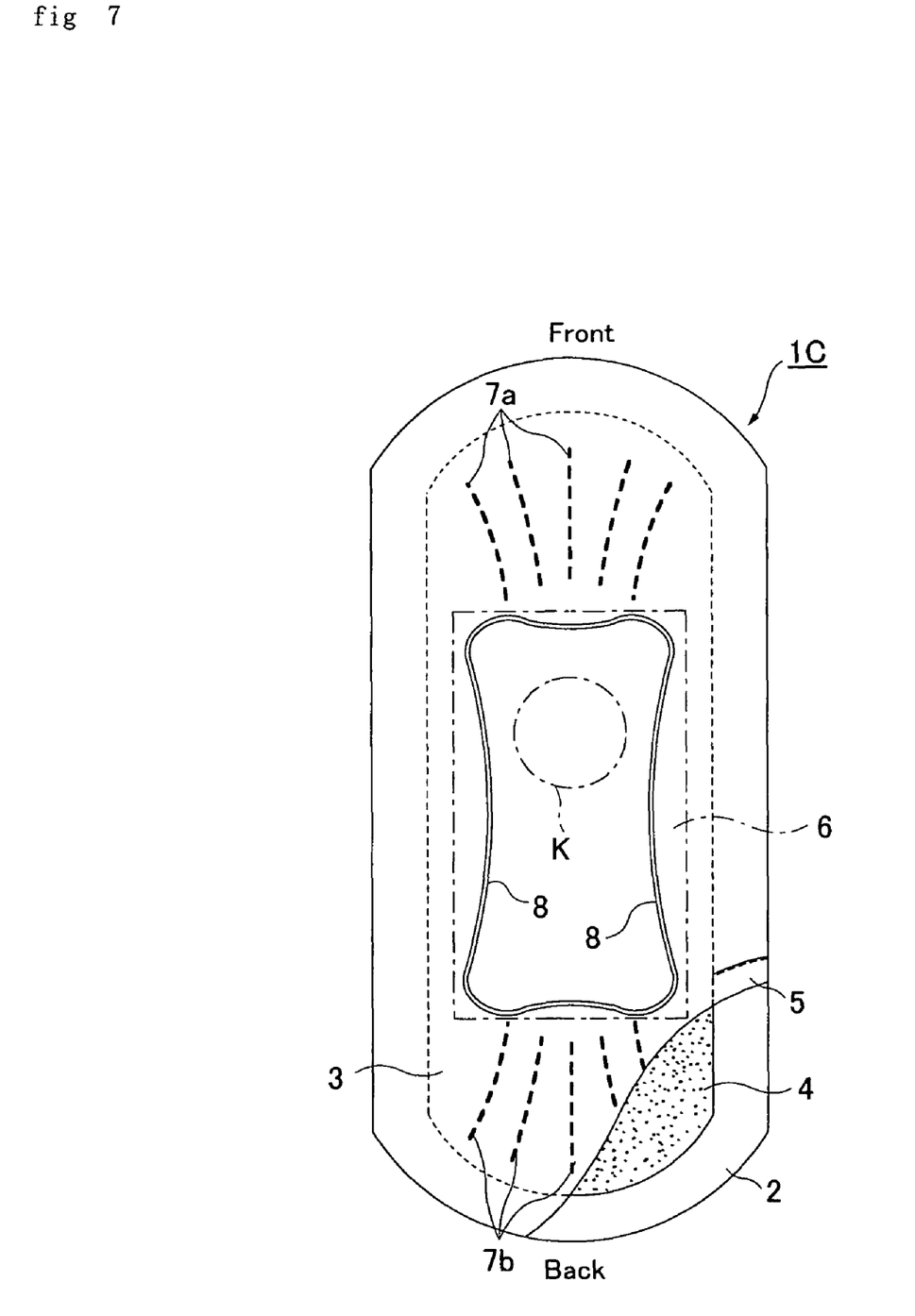
FIG. 7 is a partially fracture plan view illustrating an absorbent article IC according to a third embodiment of the present invention.

When the leakage preventing grooves 8 are formed, both the sides which sandwich the body fluid discharge area K are embossed from the upper side of the liquid permeable front sheet 3, so that a pair of the right and left concave leakage preventing grooves 8, 8 are formed in the first and second embodiments. However, the leakage preventing groove 8 may be formed on both the sides which sandwich the body fluid discharge area K so as to extend to the longitudinal direction of the product, and as shown in FIG. 7 for example, both front and rear ends of the leakage preventing grooves 8, 8 formed on the right and left sides, respectively, are bonded, so that they may be formed into an approximately square shape.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. An absorbent article, comprising:
    a liquid permeable front sheet;
    a back sheet;
    an absorbent body disposed between the liquid permeable front sheet and the back sheet, and having opposing outer absorbent body edges extending in a longitudinal direction of the absorbent body;
    said absorbent body having a standard-height portion and a middle-height portion laminated as a layer over said standard-height portion in a thickness direction of said absorbent body, said standard-height portion being on a side of the absorbent body facing the back sheet;
    said absorbent body having the middle-height portion in an approximately center area of the absorbent body;
    said middle-height portion having opposing middle-height portion side edge steps and a constant middle-height portion thickness extending from one of said opposing middle-height portion side edge steps to another one of said opposing middle-height portion side edge steps;
    said standard-height portion extending beyond both said opposing middle-height portion side edge steps to said opposing outer absorbent body edges, said standard-height portion having a constant standard-height portion thickness extending from one of said opposing outer absorbent body edges to another one of said opposing outer absorbent body edges;
    first and second leakage preventing grooves, extending in said longitudinal direction of the absorbent article which is orthogonal to a lateral direction extending between said opposing outer absorbent body edges, said first and second leakage preventing grooves being provided in the middle-height portion of the absorbent body and on either side of an area constituting a mid-portion of the middle-height portion taken in the longitudinal direction, and said first and second leakage preventing grooves having opposing side walls formed in said middle-height portion such that depths of said opposing side walls of said leakage preventing grooves are equal on opposing sides of said leakage preventing grooves; and
    each one of said first and second leakage preventing grooves having a first end portion, a second end portion and a third portion between the first end portion and second end portion, the respective third portion of said each one leakage preventing groove extending longitudinally and curving outward along a longitudinal length to be spaced farthest apart toward each of the respective first and second leakage preventing groove's first end portion and second end portion, and to be spaced gradually closer together along the longitudinal length of the respective third portions away from the respective first and second leakage preventing groove's first end portion and second end portion, the first end portion and the second end portion of each one of the first and second leakage preventing grooves curving inward and extending in the lateral direction;

each one of said first and second leakage preventing grooves extending longitudinally at positions proximate said opposing middle-height portion side edge steps of the middle-height portion so as to border the mid-portion of the middle-height portion on both longitudinally extending sides, respectively, and the leakage preventing grooves being deeper than said constant middle-height portion thickness and extending into the standard-height portion of the absorbent body.

2. The absorbent article according to claim 1, wherein a thinned portion of absorbent material is provided extending outward from said opposing middle-height portion side edge steps of the middle-height portion, said thinned portion have a thinned portion thickness less than said constant middle-height portion thickness.

3. The absorbent article according to claim 1, wherein the middle-height portion extends to first and second middle-height portion longitudinal ends and said absorbent body extends beyond said first and second middle-height portion longitudinal ends, and front and rear folds, folding the absorbent article in three into a packaging configuration, extend in said lateral direction and are respectively disposed in the standard-height portion beyond said first and second middle-height portion longitudinal ends.

4. The absorbent article according to claim 1, wherein a thickness of the standard-height portion absorbent body is 1 to 3 mm.

5. The absorbent article according to claim 4 wherein said constant middle-height portion thickness is in the range of 1.5 to 8.0 mm.

6. The absorbent article according to claim 5 wherein said leakage preventing grooves are formed in said absorbent article to have a groove depth H extending from said front sheet to a groove bottom, and said groove depth H is in the range of 0.5 to 9.0 mm 7. The absorbent article according to claim 6 wherein said leakage preventing grooves are formed in said absorbent article to have a groove depth H, and a ratio of said groove depth H to said constant standard-height portion thickness is in the range of 0.06 to 3.3.

8. The absorbent article according to claim 7 wherein said leakage preventing grooves have a bottom width B in the range of 0.5 to 5.0 mm.

9. The absorbent article according to claim 4 wherein said constant middle-height portion thickness is in the range of 2.0 to 4.0 mm.

10. The absorbent article according to claim 9 wherein said leakage preventing grooves are formed in said absorbent article to have a groove depth H extending from said front sheet to a groove bottom, and said groove depth H is in the range of 2.0 to 6.0 mm.

11. The absorbent article according to claim 10 wherein said leakage preventing grooves are formed in said absorbent article to have a groove depth H, and a ratio of said groove depth H to said constant standard-height portion thickness is in the range of 0.2 to 0.8.

12. The absorbent article according to claim 1, wherein a thickness of the standard-height portion absorbent body is 1 to 3 mm.

13. The absorbent article according to claim 12 wherein said constant middle-height portion thickness is in the range of 1.5 to 8.0 mm.

14. The absorbent article according to claim 13 wherein said leakage preventing grooves are formed in said absorbent article to have a groove depth H extending from said front sheet to a groove bottom, and said groove depth H is in the range of 0.5 to 9.0 mm.

15. The absorbent article according to claim 14 wherein said leakage preventing grooves are formed in said absorbent article to have a groove depth H, and a ratio of said groove depth H to said constant standard-height portion thickness is in the range of 0.06 to 3.3.

16. The absorbent article according to claim 15 wherein said leakage preventing grooves have a bottom width B in the range of 0.5 to 5.0 mm.

17. The absorbent article according to claim 12 wherein said constant middle-height portion thickness is in the range of 2.0 to 4.0 mm.

18. The absorbent article according to claim 17 wherein said leakage preventing grooves are formed in said absorbent article to have a groove depth H extending from said front sheet to a groove bottom, and said groove depth H is in the range of 2.0 to 6.0 mm.

19. The absorbent article according to claim 18 wherein said leakage preventing grooves are formed in said absorbent article to have a groove depth H, and a ratio of said groove depth H to said constant standard-height portion thickness is in the range of 0.2 to 0.8.

* * * * *